United States Patent

Jegham et al.

[11] Patent Number: 5,843,975
[45] Date of Patent: Dec. 1, 1998

[54] OXAZOLIDINONE DERIVATIVES, THEIR PREPARATION AND THERAPEUTICAL USE

[75] Inventors: Samir Jegham, Argenteuil; Frédéric Puech, Rueil Malmaison; Philippe Burnier, Maisons Laffitte, all of France

[73] Assignee: Synthelabo, Le Plessis Robinson, France

[21] Appl. No.: 973,246

[22] PCT Filed: May 28, 1996

[86] PCT No.: PCT/FR96/00792

§ 371 Date: Dec. 2, 1997

§ 102(e) Date: Dec. 2, 1997

[87] PCT Pub. No.: WO96/38444

PCT Pub. Date: Dec. 5, 1996

[30] Foreign Application Priority Data

Jun. 2, 1995 [FR] France ................... 95 06563
Jun. 2, 1995 [FR] France ................... 95 06564

[51] Int. Cl.$^6$ ................... A61K 31/425; C01D 413/04
[52] U.S. Cl. ................... 514/376; 514/373; 548/212; 548/231

[58] Field of Search ................... 548/212, 231; 514/373, 376

[56] References Cited

U.S. PATENT DOCUMENTS

| 5,036,090 | 7/1991 | Jarreau et al. | 514/376 |
| 5,036,091 | 7/1991 | Jarreau et al. | 514/376 |
| 5,171,747 | 12/1992 | Jarreau et al. | 514/376 |
| 5,173,490 | 12/1992 | Peglion et al. | 514/254 |
| 5,182,296 | 1/1993 | Nakai et al. | 514/376 |
| 5,196,543 | 3/1993 | Jarreau et al. | 548/232 |
| 5,235,063 | 8/1993 | Jarreau et al. | 548/232 |
| 5,332,754 | 7/1994 | Nakai et al. | 514/376 |

*Primary Examiner*—Johann Richter
*Assistant Examiner*—Laura R. C. Lutz
*Attorney, Agent, or Firm*—Jacobson, Price, Holman & Stern, PLLC

[57] ABSTRACT

The present invention relates to isoindole derivatives, and more particularly to 5-(hydroxymethyl)oxazolidine-2-one derivatives which are substituted at the 3 position by an indazole, benzisoxazole or benzisothiazole ring system, to a process for their preparation and to their application in therapy.

11 Claims, No Drawings

OXAZOLIDINONE DERIVATIVES, THEIR PREPARATION AND THERAPEUTICAL USE

This application is a 371 of PCT/FR96/00292 filed May 28, 1996.

The present invention relates to isoindole derivatives, and more particularly to 5-(hydroxymethyl)oxazolidine-2-one derivatives which are substituted at the 3 position by an indazole, benzisoxazole or benzisothiazole ring system, to a process for their preparation and to their application in therapy.

The compounds of the invention correspond to the general formula (I)

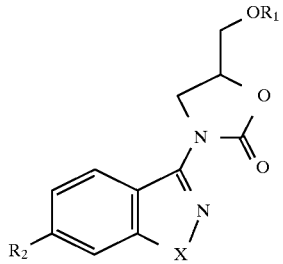

in which:
X represents an oxygen atom, a sulphur atom or a group NR, R being a hydrogen atom or a linear or branched $C_1$–$C_4$ alkyl chain,
$R_1$ represents a hydrogen atom or a methyl group, and
$R_2$ represents:
(i) a group $R_3O$ in which $R_3$ represents alternatively a hydrogen atom, or a benzyl group which is optionally substituted with a halogen atom or with a nitro or methylenedioxy group, or represents a methoxyethyl, butyl, 4,4,4-trifluorobutyl, 4,4,4-trifluoro-3-hydroxybutyl or 4,4,4-trifluorobut-2-enyl group, or (ii) a group —CH=CH—$R_4$ or —CH$_2$—CH$_2$—$R_4$, in which $R_4$ represents a hydrogen atom or a phenyl, 3,3,3-trifluoropropyl or 3,3,3-trifluoro-2-hydroxypropyl group.

The compounds of formula (I) comprise one or two asymmetric carbon atoms. They can therefore exist in the form of enantiomers or diastereoisomers. These various forms and their mixtures, including the racemic mixtures, are part of the invention.

The compounds of formula (I) in which X is an oxygen atom and $R_2$ represents a group —CH=CH—$R_4$, with the exception of compounds in which $R_4$ is a hydrogen atom, exist in the form of cis or trans isomers. These forms and their mixtures are part of the invention.

The compounds of formula (I) in which $R_2$ represents a group $OR_3$ in which $R_3$ represents the 4,4,4-trifluorobut-2-enyl group exist in the form of cis or trans isomers. These forms and their mixtures are part of the invention.

Preferred compounds are those for which:
X represents an oxygen atom, a sulphur atom or a group NR, R being a hydrogen atom or a linear or branched $C_1$–$C_4$ alkyl chain,
$R_1$ represents a methyl group or a hydrogen atom, and
$R_2$ represents a group $R_3O$ in which $R_3$ represents alternatively a hydrogen atom, or a benzyl group which is optionally substituted with a halogen atom or with a nitro or methylenedioxy group, or represents a methoxyethyl, butyl, 4,4,4-trifluorobutyl, 4,4,4-trifluoro-3-hydroxybutyl or 4,4,4-trifluorobut-2-enyl group, in the form of enantiomers or diastereoisomers, or of mixtures of these various forms, including racemic mixtures.

Other preferred compounds are those for which:
X represents an oxygen atom, a sulphur atom or a group NR, R being a hydrogen atom or a linear or branched $C_1$–$C_4$ alkyl chain,
$R_1$ represents a methyl group or a hydrogen atom, and
$R_2$ represents a group —CH=CH—$R_4$ or —CH$_2$—CH$_2$—$R_4$, in which $R_4$ represents a hydrogen atom, or a phenyl, 3,3,3-trifluoropropyl or 3,3,3-trifluoro-2-hydroxypropyl group, in the form of enantiomers or diastereoisomers, or of mixtures of these various forms, including racemic mixtures.

The compounds of choice are those for which:
X represents an oxygen atom,
$R_1$ represents a methyl group or a hydrogen atom, and
$R_2$ represents:
(i) a group $R_3O$ in which $R_3$ represents alternatively a hydrogen atom, or a benzyl group which is optionally substituted with a halogen atom or with a nitro or methylenedioxy group, or represents a methoxyethyl, butyl, 4,4,4-trifluorobutyl, 4,4,4-trifluoro-3-hydroxybutyl or 4,4,4-trifluorobut-2-enyl group, or
(ii) a group —CH=CH—$R_4$ or —CH$_2$—CH$_2$—$R_4$, in which $R_4$ represents a hydrogen atom, or a phenyl, 3,3,3-trifluoropropyl or 3,3,3-trifluoro-2-hydroxypropyl group, in the form of enantiomers or diastereoisomers, or of mixtures of these various forms, including racemic mixtures.

Among the latter, mention may be made of compounds for which:
X represents an oxygen atom,
$R_1$ represents a methyl group or a hydrogen atom, and
$R_2$ represents alternatively a hydroxyl group, or a phenylmethoxy group which is optionally substituted with a halogen atom or with a nitro or methylenedioxy group, or represents a 4,4,4-trifluorobutoxy group or a 4,4,4-trifluoro-3-hydroxybutoxy group, in the form of enantiomers or diastereoisomers, or of mixtures of these various forms, including racemic mixtures,
and, very particularly, mention may be made of (S)-5-methoxymethyl-3-[6-(4,4,4-trifluorobutoxy)-1,2-benzisoxazol-3-yl]oxazolidin-2-one.

The compounds of formula (I) in which $R_1$ is a methyl group and $R_2$ is a group $OR_3$ can be prepared according to the process represented in scheme 1. According to this process, the isoindole derivative of formula (II) is treated with one of the 4(R) or 4(S) isomers of 4-methoxymethyl-1,3-dioxolan-2-one of formula (IIIa) in the presence of potassium carbonate in order to obtain the 5(S) or 5(R) isomer of the compound of formula (Ia) according to the invention. It is then possible to debenzylate the compound (Ia) by catalytic hydrogenation under conditions which are conventional to the person skilled in the art, or with the aid of a Lewis acid such as aluminium chloride, in order to obtain the 5(S) or 5(R) isomer of the compound of formula (Ib) according to the invention. Subsequently, it is possible to treat the compound (Ib) either with a compound of formula $R_3Y$ in which $R_3$ is defined as in formula (I) above, with the exception of the meanings hydrogen and unsubstituted benzyl, and Y is a leaving group, such as a chlorine or bromine atom or a tosyloxy group, in the presence of potassium carbonate, or with a compound of formula $R_3OH$ in which $R_3$ is defined as above, in the presence of triphenylphosphine and diethyl azodicarboxylate, in order to obtain the 5(S) or 5(R) isomers of the compounds of formula (Ic) according to the invention in which $R_3$ is defined as above. In each of the compounds of formulae (II), (Ia), (Ib) and (Ic) mentioned above, X has one of the meanings given in the formula (I) and Bn represents the benzyl group.

The compounds of formula (I) for which X represents an NH group can be prepared from the compounds of formula (Ic) in which X represents an $NCH_3$ group by demethylation with the aid of benzoyl peroxide.

The compounds of formula (I) in which $R_1$ is a methyl group and $R_2$ is a group —CH=CH—$R_4$ or a group —$CH_2$—$CH_2$—$R_4$ can be prepared according to the process represented in scheme 2. According to this process, the compound of formula (Ib) according to the invention is treated with trifluoromethanesulphonic anhydride. The compound of formula (IV) thus obtained is reacted with tributylvinyl tin in the presence of lithium chloride and tetrakis (triphenylphosphine)palladium. The compound of formula (Id) according to the invention is then treated with ozone, and then with dimethylsulphide in dichloromethane, and the compound of formula (V) obtained is reacted with a triphenylphosphonium iodide of formula $R_4CH_2PPh_3$ $^{+/-}$ in which $R_4$ is defined as in formula (I) above, with the exception of the meaning hydrogen, in the presence of potassium carbonate. The compound of formula (Ie) according to the invention in which $R_4$ is defined as above is then reduced with hydrogen in the presence of a catalyst in order to obtain the compound of formula (If) according to the invention in which $R_4$ is defined as above. In each of the compounds (Ib), (IV), (Id), (V), (Ie) and (If), X is as defined in formula (I) above.

The compounds of formula (I) in which R, is a hydrogen atom and $R_2$ is a group $OR_3$, where $R_3$ is defined as in formula (I) above, can be prepared according to the process represented in scheme 3. According to this process, the compound of formula (II) is treated with one of the 4(R) or 4(S) isomers of 4-phenylmethoxymethyl-1,3-dioxolan-2-one (IIIb) in the presence of potassium carbonate in order to obtain the 5(S) or 5(R) isomer of the compound of formula (VI). The isomer of formula (VI) is debenzylated by catalytic hydrogenation to give the 5(S) or 5(R) isomer of the compound of formula (Ib) as defined above. The latter compound is subsequently treated with a compound of formula $R_3Y$ in which $R_3$ is defined as in formula (I) above, with the exception of the meaning hydrogen, and Y is a leaving group such as a chlorine or bromine atom or a tosyloxy group, to give the 5(S) or 5(R) isomers of the compounds of formula (Ic) according to the invention in which $R_3$ is defined as above. In all of the compounds (II), (Ib), (Ic) and (VI) defined above, X is defined as in formula (I) above.

The compounds (Ig) for which $R_1$ represents a hydrogen atom and $R_2$ is a group —CH=CH—$R_4$ or —$CH_2$—$CH_2$—$R_4$ are prepared by demethylation of the compounds (If) according to the invention with the aid of boron tribromide according to the process described in scheme 2.

The compound of formula (II) is prepared according to the process represented in scheme 4. According to this process, 2-fluoro-4-hydroxybenzonitrile is treated with benzyl bromide in the presence of potassium carbonate. The 2-fluoro-4-phenylmethoxybenzonitrile thus obtained is subsequently treated by three different routes depending on the meaning of X:

when X represents an oxygen atom: 2-fluoro-4-phenylmethoxybenzonitrile is treated with acetone oxime in the presence of potassium t-butanolate in order to prepare 2-[[(1-methylethylidene)amino]oxy]-4-phenylmethoxybenzonitrile, which is reacted with a solution of hydrochloric acid in ethanol, when X represents an sulphur atom: 2-fluoro-4-phenylmethoxybenzonitrile is treated with sulphur and ammonia in propanol, when X represents a group NR, R being a linear or branched $C_1$–$C_4$ alkyl chain, 2-fluoro-4-phenylmethoxybenzonitrile is treated with $R_5NHNH_2$, in which $R_5$ is a linear or branched $C_1$–$C_4$ alkyl chain, in ethanol.

Each of these routes leads to the preparation of a compound of formula (VII) in which X represents an oxygen atom, a sulphur atom or a group NR, R being a linear or branched $C_1$–$C_4$ alkyl chain. The compound of formula (VII) is treated with ethyl chloroformate in the presence of sodium hydrogen carbonate to give the compound of formula (II) in which X is defined as above.

The 4(S) isomer of the compound of formula (IIIa) is a known compound whose preparation is described in the patent EP-0 511 031. Its 4(R) isomer is prepared according to the same method from (R)-2,2-dimethyl-1,3-dioxolane-4-methanol.

The 4(S) isomer of the compound of formula 4(R)-phenylmethoxymethyl-1,3-dioxolan-2-one (IIIb) is a known compound whose preparation is described in Helvetica Chimica Acta, 66, 1210–1240 (1983). Its 4(R) isomer is prepared according to the same method from (R)-2,2-dimethyl-1,3-dioxolane-4-methanol.

The examples which follow illustrate the present invention.

Example 1

(S)-5-Methoxymethyl-3-[1-methyl-6-(phenylmethoxy)-1H-indazol-3-yl]oxazolidine-2-one 1.1. (R)-4-Methoxymethyl-2,2-dimethyl-1-3-dioxolane 420 ml of demineralized water and 420 g (10.5 mol) of sodium hydroxide pellets are introduced into a 6-liter reactor fitted with a condenser, a temperature probe and a dropping funnel. 2.3 l of dichloromethane, 396 g (3.00 mol) of (R)-2,2-dimethyl-1,3-dioxolane-4-methanol ($[\alpha]_D^{20}$=−11° ; c=4; methanol) and 20.5 g (0.090 mol) of benzyltriethylammonium chloride are added to the solution with stirring at 20° C. 567 g (4.50 mol) of dimethyl sulphate are then added over 50 minutes while maintaining the temperature below 30° C. The mixture is stirred for 18 hours and then 1 liter of water is added. The organic phase is separated off and washed with 0.5 l of water. The aqueous phases are reextracted with 3 l of dichloromethane and then the organic phases are combined, filtered and concentrated by distillation under reduced pressure. 496 g of product are obtained.

1.2. (S)-3-Methoxypropane-1,2-diol

A mixture of 496 g of the product obtained in the preceding stage in 220 ml of demineralized water is heated to 60° C. with stirring and then 1.5 ml of 36% hydrochloric acid are added. Heating is maintained for 40 minutes and then the medium is adjusted to pH 8–9 by addition of 19 ml of triethylamine. The solvent is evaporated under a pressure of 5.2 kPa and at a temperature lower than 70° C. and then the residue is distilled at 61° C. under a pressure of 13 Pa. 246 g of product are obtained.

$[\alpha]_D^{20}$=+5.8° (c=4 ;methanol).

1.3. (R)-4-Methoxymethyl-1,3-dioxolan-2-one 245 g (3.31 mol) of (S)-3-methoxypropane-1,2-diol and 560 ml (4.62 mol) of diethylcarbonate are introduced into a round-bottomed flask fitted with a dropping funnel and a top-mounted distillation apparatus. The mixture is heated to 95°

C. and then a solution of sodium methylate, obtained from 10 ml of methanol and 0.5 g (0.02 mol) of sodium, is added. The ethanol formed during the reaction (mass temperature: 95° to 112° C.; column temperature: 82° to 78° C.) is distilled for 2 hours and then the mixture is cooled and distilled under a pressure of 13 Pa in order to separate off the excess diethyl carbonate. 267 g of product are obtained.

$[\alpha]_D^{20}$=+30.3° (c=1; dichloromethane).

1.4. 2-Fluoro-4-(phenylmethoxy)benzonitrile 15.2 ml (0.127 mol) of benzyl bromide and 29.3 g (0.212 mol) of potassium carbonate are added to a solution of 13.3 g (0.106 mol) of 2-fluoro-4-hydroxybenzonitrile in 150 ml of acetonitrile. The mixture is stirred at reflux for 1 hour 30 minutes and then filtered, the filtrate is concentrated under reduced pressure, and the oil obtained is diluted in the minimum amount of dichloromethane. After crystallization by addition of diisopropyl ether, filtration and drying, 20.3 g of product are obtained. Melting point : 87° C.

1.5. 1-Methyl-6-(phenylmethoxy)-1H-indazol-3-amine 20 g (0.088 mol) of 2-fluoro-4-(phenylmethoxy)benzonitrile are heated at reflux with 60 ml of a solution of ethanol and 15.45 ml (0.29 mol) of a solution of methylhydrazine for 11 hours. The mixture is chilled and then filtration is carried out. The material on the frit is washed first with ethanol and secondly with ether. 20.2 g of product are obtained.

Melting point: 150° C.

1.6. Ethyl [1-methyl-6-(phenylmethoxy)-1H-indazol-3-yl] carbamate 9.8 g of sodium hydrogen carbonate (0.117 mol) are added to a solution of 19.7 g (0.078 mol) of 1-methyl-6-(phenylmethoxy)-1H-indazol-3-amine in 200 ml of a 9:1 mixture of tetrahydrofuran/water, and then 8.9 ml (0.093 mol) of ethyl chloroformate are added dropwise while maintaining the temperature at 25° C. A milky suspension is obtained which is left with stirring for 30 minutes, and then the solvent is evaporated off under reduced pressure. The residue is treated with dichloromethane and water. The organic phase is decanted off, dried over sodium sulphate and concentrated under reduced pressure. The product is crystallized from diisopropyl ether. 20.1 g of product are obtained.

Melting point: 204° C.

1.7. (S)-5-Methoxymethyl-3-[1-methyl-6-(phenylmethoxy)-1H-indazol-3-yl]oxazolidin-2-one A mixture of 1.03 g (7.8 mmol) of (R)-4-methoxymethyl-1,3-dioxolan-2-one and 82 mg (0.6 mmol) of potassium carbonate in 30 ml of anhydrous dimethylformamide is heated to 135° C. and then a solution of 1.95 g (6 mmol) of ethyl [1-methyl-6-(phenylmethoxy)-1H-indazol-3-yl] carbamate in 30 ml of dimethylformamide is added over 20 minutes. The reaction medium is stirred at 135° C. for 45 minutes and then cooled, and the solvent is evaporated off under reduced pressure. The residue is purified on a silica column with a 50:50 mixture of ethyl acetate and cyclohexane. The product is isolated in the form of an oil which crystallizes and which is triturated in diisopropyl ether. 1.5 g of product are obtained.

Melting point: 116°–117° C.

$[\alpha]_D^{20}$=+26.10 (c=1; methanol)

Example 2

(S)-3-(6-Hydroxy-1-methyl-1H-indazol-3-yl)-5-(methoxymethyl)oxazolidin-2-one 3.1 g (8.4 mmol) of (S)-5-(methoxymethyl)-3-[1-methyl-6-(phenylmethoxy)-1H-indazol-3-yl]oxazolidine-2-one are hydrogenated in 40 ml of tetrahydrofuran and 40 ml of ethanol in the presence of 500 mg of 10% palladium on carbon (containing 50% moisture). After filtration of the catalyst and evaporation of the solvent under reduced pressure the residue is purified by chromatography on a silica column with dichloromethane, and 2.1 g of product are obtained.

Melting point: 50°–55° C.

$[\alpha]_D^{20}$=+33.8° (c=1, methanol)

Example 3

(S)-5-Methoxymethyl-3-[1-methyl-6-(4,4,4-trifluorobutoxy)-1H-indazol-3-yl]oxazolidin-2-one A mixture of 524 mg (2 mmol) of (S)-3-(6-hydroxy-1-methyl-1H-indazol-3-yl)-5-(methoxymethyl) oxazolidin-2-one, 478 mg (2.5 mmol) of 4,4,4-trifluoro-1-bromobutane and 552 mg (4 mmol) of potassium carbonate in 10 ml of acetonitrile is stirred at reflux for 3 hours. The mixture is then cooled and filtered, the solvent is evaporated off under reduced pressure, and the residue is purified by recrystallization from an isopropanol/diisopropyl ether mixture. 0.4 g of product is obtained in the form of a white powder.

Melting point: 103°–104°

$[\alpha]_D^{20}$=+25.6° (c=1, methanol)

Example 4

(S)-5-Methoxymethyl-3-[6-(4,4,4-trifluorobutoxy)-1H-indazol-3-yl]oxazolidin-2-one A mixture of 0.30 g (0.77 mol) of (S)-5-methoxymethyl-3-[1-methyl-6-(4,4,4-trifluorobutoxy)-1H-indazol-3-yl] oxazolidin-2-one and 0.47 g (1.9 mol) of benzoyl peroxide in 10 ml of dichloromethane is refluxed for 12 hours. The solvent is evaporated off under reduced pressure, the residue is taken up in methanol, and the insoluble material is filtered off. 4 ml of 1N sodium hydroxide solution are then added. The mixture is stirred for 15 minutes. The product is isolated by filtration and recrystallized from n-butanol. 0.20 g of product is obtained.

Melting point: 184.9° C.–185.3° C.

$[\alpha]_D^{20}$=+11.6° (c=1; dimethyl sulphoxide)

Example 5

(S)-5-Methoxymethyl-3-[6-(phenylmethoxy)-1,2-benzisoxazol-3-yl]oxazolidin-2-one 5.1. 2-[[(1-Methylethylidene)amino]oxy]-4-(phenylmethoxy)benzonitrile A solution of 7.83 g (0.107 mol) of acetone oxime in 200 ml of dimethylformamide is stirred for 30 minutes in the presence of 12 g (0.11 mol) of 95% potassium t-butanolate. A solution of 20.3 g (0.089 mol) of 2-fluoro-4-(phenylmethoxy)benzonitrile in 100 ml of dimethylformamide is then added over 15 minutes. The mixture is stirred for 2 hours and then poured into ice-water. The crystalline product is filtered off and dissolved in dichloromethane, and the solution is then dried over sodium sulphate and concentrated under reduced pressure. 21.2 g of product are obtained.

Melting point: 102° C.

5.2. 6-(Phenylmethoxy)-1,2-benzisoxazol-3-ylamine 20.2 g (0.072 mol) of 2-[[(1-methylethylidene) amino] oxy]-4-(phenylmethoxy)benzonitrile are reacted with 340 ml of a 4N solution of hydrochloric acid in ethanol for 20 hours and then the solvent is evaporated. The crystalline product is subsequently triturated in dichloromethane, then the mixture is filtered and the solid is dissolved in the minimum amount of lukewarm methanol. The solution is alkalified with ammonia and then diluted with water. After filtration and washing with water, 16.3 g of product are obtained.

Melting point: 166° C.

5.3. Ethyl [6-(phenylmethoxy)-1,2-benzisoxazol-3-yl] carbamate 8.8 ml (0.092 mol) of ethyl chloroformate and 10.6 g (0.126 mol) of sodium hydrogen carbonate are added to a solution of 10.1 g (0.042 mol) of 6-(phenylmethoxy)-1,2-benzisoxazol-3-amine in 100 ml of a 9:1 mixture of tetrahydrofuran and water. The mixture is stirred for 18 hours and then the solvent is evaporated off and the residue is treated with dichloromethane and water. The organic phase is decanted off, dried over sodium sulphate and concentrated under reduced pressure. After crystallization from isopropyl alcohol and recrystallization from n-butanol, 11.5 g of product are obtained.

Melting point: 144°–146° C.

5.4. (S)-5-Methoxymethyl-3-[6-(phenylmethoxy)-1,2-benzisoxazol- 3-yl]oxazolidin-2-one A mixture of 4.5 g (0.034 mol) of 4(R)-methoxymethyl-1,3-dioxolan-2-one and 0.24 g (1.7 mmol) of potassium carbonate in 35 ml of anhydrous dimethylformamide is heated to 140° C. and then a solution of 5.5 g (18 mmol) of ethyl 6-(phenylmethoxy)-1,2-benzisoxazole-3-carbamate in 20 ml of dimethylformamide is added over 20 minutes. The medium is stirred at 140° C. for 40 minutes and then cooled, and the solvent is evaporated off under reduced pressure. The residue is purified on a silica column with a 30:70 mixture of ethyl acetate and cyclohexane. After crystallization from diisopropyl ether, 4.1 g of product are obtained.

Melting point: 92.0°–92.1° C.

$[\alpha]_D^{\circ}=+8.6°$ (c=1; dichloromethane).

Example 6

(S)-3-(6-Hydroxy-1,2-benzisoxazol-3-yl)-5-(methoxymethyl)oxazolidin-2-one

A solution of 3.9 g (0.011 mol) of (S)-5-methoxymethyl-3-[6-(phenylmethoxy)-1,2-benzisoxazol-3-yl]oxazolidin-2-one in 60 ml of tetrahydrofuran and 60 ml of ethanol is hydrogenated for 30 minutes in the presence of 1.1 g of 5% palladium on carbon (containing 50% moisture). The catalyst is then filtered off and the filtrate is evaporated under reduced pressure. 2.3 g of product are obtained.

Melting point: 148.7°–148.8° C.

$[\alpha]_D^{20}=+14.2°$ (c=1; dimethyl sulphoxide).

Example 7

(S)-5-Methoxymethyl-3-[6-(4,4,4-trifluorobutoxy)-1,2-benzisoxazol-3-yl]oxazolidin-2-one A mixture of 1.3 g (4.9 mmol) of (S)-3-(6-hydroxy-1,2-benzisoxazol-3-yl)-5-methoxymethyl-oxazolidin-2-one, 1.4 g (7.3 mmol) of 4-bromo-1,1,1-trifluorobutane and 1.4 g (9.8 mmol) of potassium carbonate in 20 ml of acetonitrile is stirred at reflux for 30 minutes. The mixture is subsequently cooled and filtered, the solvent is evaporated off under reduced pressure and the residue is purified by chromatography on a silica column with dichloromethane. After treatment with vegetable black in dichloromethane, 1.5 g of product are obtained.

Melting point: 120.4°–120.5° C.

$[\alpha]_D^{20}=+8.7°$ (c=1; dichloromethane).

Example 8

(R)-5-Methoxymethyl-3-[6-(phenylmethoxy)-1,2-benzisoxazol-3-yl]oxazolidin-2-one

A mixture of 1.4 g (0.010 mol) of 4(S)-methoxymethyl-1,3-dioxolan-2-one and 0.1 g (0.00073 mol) of potassium carbonate in 35 ml of anhydrous dimethylformamide is heated to 140° C. and then a solution of 2.5 g (0.0080 mol) of ethyl 6-(phenylmethoxy)-1,2-benzisoxazole-3-carbamate in 10 ml of dimethylformamide is added over 20 minutes. The medium is stirred at 140° C. for 35 minutes and then cooled, and the solvent is evaporated off under reduced pressure. The residue is purified on a silica column with a 25:75 mixture of ethyl acetate and cyclohexane. After crystallization from diisopropyl ether, 1.65 g of product are obtained.

Melting point: 92.0°–92.2° C.

$[\alpha]_D^{20}=-9.6°$ (c=1; dichloromethane).

Example 9

(R)-3-(6-Hydroxy-1,2-benzisoxazol-3-yl)-5-(methoxymethyl)oxazolidin-2-one

A solution of 21 g (0.059 mol) of (R)-5-methoxymethyl-3-[6-(phenylmethoxy)-1,2-benzisoxazol-3-yl]oxazolidin-2-one in 310 ml of tetrahydrofuran and 310 ml of ethanol is hydrogenated for 30 minutes in the presence of 6 g of 5% palladium on charcoal (containing 50% moisture). The catalyst is subsequently filtered off and the filtrate is evaporated under reduced pressure. The residue is purified on a silica column with a 2% mixture of methanol in dichloromethane. 2.3 g of product are obtained.

Melting point: 151.4°–151.5° C.

$[\alpha]_D^{20}=-14.2°$ (c=1; dimethyl sulphoxide).

Example 10

(R)-5-Methoxymethyl-3-[6-(4,4,4-trifluoro-3-(R)-hydroxybutoxy)-1,2-benzisoxazol-3-yl]oxazolidin-2-one A mixture of 1.0 g (3.8 mmol) of (R)-3-( 6-hydroxy-1,2-benzisoxazol-3-yl)-5-(methoxymethyl)oxazolidin-2-one, 1.8 g (6.2 mmol) of 4,4,4-trifluoro-3(R)-hydroxybutyl tosylate and 1.0 g (7.6 mmol) of potassium carbonate in 25 ml of acetonitrile is stirred at reflux for 3 hours. The mixture is then cooled, the solvent is evaporated off under reduced pressure, and the residue is taken up in ethyl acetate and washed with water. The organic phase is dried over sodium sulphate and concentrated under reduced pressure and the product obtained is chromatographed on a silica column with a mixture of 1% methanol in dichloromethane. After recrystallization from a mixture of ethyl acetate and diisopropyl ether, 0.6 g of product is obtained.

Melting point: 147° C.

$[\alpha]_D^{20}=+16.60$ (c=1; dichloromethane).

Example 11

(S)-5-Hydroxymethyl-3-[6-(4,4,4-trifluorobutoxy)-1,2-benzisoxazol-3-yl]oxazolidin-2-one 11.1. (S)-5-Phenylmethoxymethyl-3-[6-(phenylmethoxy)-1,2-benzisoxazol-3-yl]oxazolidin-2-one A mixture of 4.2 g (0.02 mol) of (R)-4-phenylmethoxymethyl-1,3-dioxolan-2-one and 0.14 g (1.0 mmol) of potassium carbonate in 50 ml of anhydrous dimethylformamide is heated to 140° C. and then a solution of 3.1 g (1.0 mmol) of ethyl 6-(phenylmethoxy)-1,2-benzisoxazole-3-carbamate in 10 ml of dimethylformamide is added over 10 minutes. The reaction medium is stirred at 140° C. for 30 minutes and then cooled and the solvent is evaporated off under reduced pressure. The residue is purified on a silica column with a mixture of 20% ethyl acetate in cyclohexane. 2.0 g of product are obtained.

Melting point: 98°–99° C.

$[\alpha]_D^{20}$=−1.0° (c=1; dichloromethane).

11.2. (S)-5-Hydroxymethyl-3-(6-hydroxy-1,2-benzisoxazol-3-yl)oxazolidin-2-one

A solution of 1.7 g (0.040 mol) of (S)-5-phenylmethoxymethyl-3-[6-(phenylmethoxy)-1,2-benzisoxazol-3-yl]oxazolidin-2-one in 20 ml of tetrahydrofuran and 2 ml of a 3N solution of hydrochloric acid in ethanol is hydrogenated for 50 minutes in the presence of 0.5 g of 5% palladium on charcoal (containing 50% moisture). The catalyst is then filtered off and the filtrate is evaporated under reduced pressure. After trituration of the residue in dichloromethane, 0.85 g of product is obtained.

Melting point: 226°–228° C.

$[\alpha]_D^{20}$=+18.1° (c=1; dimethyl sulphoxide).

11.3. (S)-5-Hydroxymethyl-3-[6-(4,4,4-trifluorobutoxy)-1,2-benzisoxazol-3-yl]oxazolidin-2-one A mixture of 0.75 g (0.030 mol) of (S)-5-hydroxymethyl-3-(6-hydroxy-1,2-benzisoxazol-3-yl)oxazolidin-2-one, 0.63 g (3.3 mmol) of 4-bromo-1,1,1-trifluorobutane and 0.83 g (6.0 mmol) of potassium carbonate in 12 ml of dimethylformamide and 2.5 ml of acetonitrile is stirred at reflux for 1 hour and then cooled and poured into water, and the precipitate is filtered off. After washing with water and then with petroleum ether and chromatography on a silica column with a mixture of 50% ethyl acetate in dichloromethane, 0.70 g of product is obtained.

Melting point: 159.6°–159.9° C.

$[\alpha]_D^{20}$=+12.1° (c=1;dichloromethane).

Example 12

(R)-5-(Methoxymethyl)-3-(6-ethenyl-1,2-benzisoxazol-3-yl)-oxazolidin-2-one 12.1. [(R)-5-(Methoxymethyl)-2-oxo-3-oxazolidinyl]-1,2-benzisoxazol-6-yl trifluoromethanesulphonate 8.4 ml (0.050 mol) of trifluoromethanesulphonic anhydride are added at 0° C. over 10 minutes to a solution of 11 g (0.042 mol) of (R)-5-(methoxymethyl)-3-(6-hydroxy-1,2-benzisoxazol-3-yl)oxazolidine-2-one in 110 ml of pyridine. The solution is stirred for 18 hours and then poured into ice-cold 2N aqueous hydrochloric acid solution. The product is extracted with ethyl acetate and then the organic phase is dried over sodium sulphate and concentrated under reduced pressure. 16.5 g of product are obtained.

Melting point: 94° C.

12.2. (R)-5-(Methoxymethyl)-3-(6-ethenyl-1,2-benzisoxazol-3-yl)oxazolidin-2-one

A mixture of 14.9 g (0.038 mol) of [(R)-5-(methoxymethyl)-2-oxo-3-oxazolidinyl]-1,2-benzisoxazol-6-yl trifluoromethanesulphonate, 12.3 g (0.038 mol) of tributylvinyl tin, 765 mg (0.66 mmol) of tetrakis (triphenylphosphine)palladium and 4.8 g (0.11 mol) of lithium chloride in 160 ml of dioxane is stirred at reflux for 2 hours. The solvent is subsequently evaporated off under reduced pressure, the residue is taken up in ethyl acetate, the mixture is filtered over silica, and the organic phase is washed with water, dried over sodium sulphate and concentrated under reduced pressure. The oil obtained is redissolved in acetonitrile and the solution is washed with hexane and concentrated. By chromatography of the residue on a silica column with a mixture of 30% ethyl acetate in cyclohexane, 16.5 g of product are obtained.

Melting point: 79.2°–79.4° C.

$[\alpha]_D^{20}$=−5.4° (c=1; dichloromethane).

Example 13 trans-(R)-5-(Methoxymethyl)-3-[6-(5,5,5-trifluoro-4(R)-hydroxypent-1-enyl)-1,2-benzisoxazol-3-yl]oxazolidin-2-one 13.1. (R)-5-Methoxymethyl-3-(6-formyl-1,2-benzisoxazol-3-yl)oxazolidin-2-one A stream of ozone at −40° C. is passed for 2 hours into a solution of 8.0 g (0.029 mol) of (R)-5-(methoxymethyl)-3-(6-ethenyl-1,2-benzisoxazol-3-yl)oxazolidin-2-one in 210 ml of dichloromethane, then the ozone is driven off with a stream of argon, and 10.7 ml (0.15 mol) of dimethyl sulphide are added. The mixture is stirred for 3 hours while allowing the temperature to return to ambient temperature, and then the solvent is evaporated off under reduced pressure. By chromatography of the residue on a silica column with a mixture of 30% ethyl acetate in cyclohexane, 5.0 g of product are obtained.

Melting point: 116° C.

13.2. trans-(R)-5-(Methoxymethyl)-3-[6-(5,5,5-trifluoro-4(R)-hydroxypent-1-enyl)-1,2-benzisoxazol-3-yl)oxazolidin-2-one A mixture of 1.8 g (6.5 mmol) of (R)-5-methoxymethyl-3-(6-formyl-1,2-benzisoxazol-3-yl)oxazolidin-2-one, 4.0 g (7.8 mmol) of (4,4,4-trifluoro-3(R)-hydroxybutyl) triphenylphosphonium iodide and 1.25 g (9.1 mmol) of potassium carbonate in 1.4 ml of formamide and 18 ml of dioxane is stirred at reflux for 2 hours and then poured into ice-water. The product is subsequently extracted with ethyl acetate, and the organic phase is dried over sodium sulphate and concentrated under reduced pressure. After chromatography of the residue on a silica column with a mixture of 30% ethyl acetate and cyclohexane and trituration in diisopropyl ether, 1.2 g of product are obtained.

Melting point: 141.1°–141.6° C.

$[\alpha]_D^{20}$=+15.8° (c=1; dichloromethane)

Example 14

(R)-5-(Methoxymethyl)-3-[6-(5,5,5-trifluoro-4(R)-hydroxypentyl)-1,2-benzisoxazol-3-yl]oxazolidin-2-one A mixture of 1.0 g (0.0026 mol) of trans-(R)-5-(methoxymethyl)-3-[6-(5,5,5-trifluoro-4(R)-hydroxy-1-pentenyl)-1,2-benzisoxazol-3-yl]oxazolidin-2-one in 30 ml of ethanol is hydrogenated for 30 minutes in the presence of 0.22 g of 5% palladium on charcoal containing 50% water. After filtration, the filtrate is concentrated under reduced pressure. By chromatography of the residue on a silica column of a mixture of 1.5% methanol in dichloromethane and trituration in a mixture of petroleum ether and diisopropyl ether, 0.88 g of product is obtained.

Melting point: 129.0°–129.4° C.

$[\alpha]_D^{20}$=+4.9° (c=1; dichloromethane).

Example 15

(R)-5-Hydroxymethyl-3-[6-(5,5,5-trifluoro-4-(R)hydroxypentyl)-1,2-benzisoxazol-3-yl]oxazolidin-2-one 3.8 ml (3.8 mmol) of a 1M solution of boron tribromide in dichloromethane are added dropwise at 0° C. to a solution of 0.495 g (1.27 mmol) of (R)-5-(methoxymethyl)-3-[6-(5,5,5-trifluoro-4(R)-hydroxypentyl)-1,2-benzisoxazol-3-yl]oxazolidin-2-one in 5 ml of dichloromethane. After reaction for 2 hours, the medium is diluted with dichloromethane and treated with dilute ammonia until it has a slightly basic pH. The organic phase is separated off, dried over sodium sulphate and evaporated. By chromatography on a silica column with a mixture of ethyl acetate and cyclohexane followed by trituration in ethyl acetate, 0.12 g of product is obtained.

Melting point: 135.1°–136.2 ° C.
$[\alpha]_D^{20}=0.0°$ (c=1; methanol).

Example 16

(S)-5-Methoxymethyl-3-[6-(phenylmethoxy)-1,2-benzisothiazol-3-yl]oxazolidin-2-one 16.1. 6-(Phenylmethoxy)-1,2-benzisothiazol-3-amine A mixture of 13.2 g (0.058 mol) of 2-fluoro-4-(phenylmethoxy)benzonitrile and 1.85 g (0.058 mol) of sulphur in 15 ml (0.58 mol) of ammonia and 50 ml of methylglycol is brought to 100° C. in an autoclave over 5 hours. The methylglycol is subsequently evaporated off under reduced pressure. The mixture is taken up in dichloromethane, the insoluble material is filtered off, and then the solvent is evaporated off under reduced pressure. The product is purified by chromatography on a silica column with cyclohexane and ethyl acetate in proportions of 60:40. Subsequently, a second purification by chromatography on a silica column with a mixture of diisopropyl ether and methanol in proportions of 99:1 leads to 1.7 g of product.

Melting point: 158° C.

16.2. Ethyl [6-(phenylmethoxy)-1,2-benzisothiazol-3-yl]carbamate

According to the process of Example 1.6., 1.19 g of ethyl [6-(phenylmethoxy)-1,2-benzisothiazol-3-yl]carbamate are obtained from 1.28 g (0.005 mol) of 6-(phenylmethoxy)-1,2-benzisothiazol-3-amine.

Melting point: 149°–150° C.

16.3. (S)-5-Methoxymethyl-3-[6-(phenylmethoxy)-1,2-benzisothiazol-3-yl]oxazolidin-2-one According to the process described in Example 1.7., 0.4 g of (S)-5-methoxymethyl-3-[6-(phenylmethoxy)-1,2-benzisothiazol-3-yl]oxazolidin-2-one, is obtained from 0.57 g (1.73 mmol) of ethyl [6-(phenylmethoxy)-1,2-benzisothiazol-3-yl]carbamate, 0.29 g (2.2 mmol) of (R)-4-methoxymethyl-1,3-dioxolan-2-one, and 24 mg (0.17 mmol) of potassium carbonate.

Melting point: 105°–106° C.
$[\alpha]_D^{20}=+9.9°$ (c=1; methanol)

Example 17

(S)-5-Methoxymethyl-3-[6-(4,4,4-trifluorobutoxy)-1,2-benzisothiazol-3-yl]oxazolidin-2-one 17.1. (S)-5-Methoxymethyl-3-(6-hydroxy-1,2-benzisothiazol-3-yl)oxazolidin-2-one 8.7 ml (68 mmol) of dimethylaniline and 6.9 g (0.051 mol) of aluminium chloride are added in three portions over 4 hours to a solution of 2.10 g (5.67 mmol) of (S)-5-methoxymethyl-3-[6-(phenylmethoxy)-1,2-benzisothiazol-3-yl]oxazolidin-2-one in 76 ml of dichloromethane, which solution is cooled at −8° C. The mixture is poured into ice-water and the product is extracted with dichloromethane. The organic phase is dried over sodium sulphate and concentrated under reduced pressure. After purification by chromatography on a silica column with dichloromethane and methanol, in proportions of 99:1, and trituration in diisopropyl ether, 1.4 g of product are obtained.

Melting point: 142°–143° C.

17.2. (S)-5-Methoxymethyl-3-[6-(4,4,4-trifluorobutoxy)-1,2-benzisothiazol-3-yl]oxazolidin-2-one According to the process of Example 3, 0.42 g of (S)-5-methoxymethyl-3-[6-(4,4,4-trifluorobutoxy)-1,2-benzisothiazol-3-yl]oxazolidin-2-one is obtained from 0.4 g (1.43 mmol) of (S)-5-methoxymethyl-3-(6-hydroxy-1,2-benzisothiazol-3-yl)oxazolidin-2-one, 0.34 g (1.25 mmol) of 4,4,4-trifluorobutyl bromide and 0.42 g (3.1 mmol) of potassium carbonate in 8 ml of acetonitrile.

Melting point: 78°–79° C.
$[\alpha]_D^{20}=+8.9°$ (c=1; methanol).

The following table collates some compounds according to the invention with their physical characteristics.

The configuration designated R and/or S, and also 5R and/or 5S, refers to the oxazolidinone heterocycle, and the configuration designated 3R, 3S and 4R refers to the chain $R_2$.

TABLE

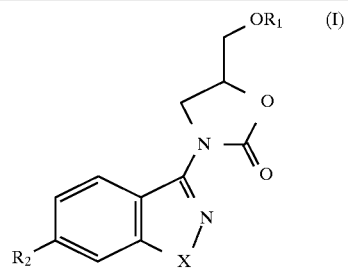

(I)

| No. | X | $R_1$ | $R_2$ | Config. | m.p. (°C.) | $[\alpha]_D^{20}$ c = 1; $CH_2Cl_2$ |
|---|---|---|---|---|---|---|
| 1 | O | Me | Bn—O | R | 92.0–92.2 | −9.6° |
| 2 | O | Me | Bn—O | S | 92.0–92.1 | +8.6° |
| 3 | O | Me | H—O | R | 151.4–151.5 | −14.2° |
| 4 | O | Me | H—O | S | 148.7–148.8 | +14.2° |
| 5 | O | Me | $F_3C$—CHOH—$(CH_2)_2$—O | 3R,5R | 147.0 | +16.6 |

TABLE-continued

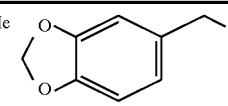

(I)

| No. | X | $R_1$ | $R_2$ | Config. | m.p. (°C.) | $[\alpha]_D^{20}$ c = 1; $CH_2Cl_2$ |
|---|---|---|---|---|---|---|
| 6 | O | Me | (methylenedioxybenzyl-O) | R | 106.0–107.2 | −7.5° |
| 7 | O | H | H—O | S | 226–228 | +18.1° |
| 8 | O | H | Bn—O | R | 166.3–166.8 | −14.0° |
| 9 | O | H | $F_3C-(CH_2)_3-O$ | S | 159.6–159.9 | +12.1° |
| 10 | O | Me | $F_3C-(CH_2)_3-O$ | S | 120.4–120.5 | +8.7° |
| 11 | O | Me | $F_3C-(CH_2)_3-O$ | R | 132–133 | −11.2° |
| 12 | O | Me | 3-Cl—Bn—O | R | 143.5–144.1 | −7.5° |
| 13 | O | Me | 4-Cl—Bn—O | R | 178.7 | −8.6° |
| 14 | O | Me | 4-F—Bn—O | R | 145.8–146.0 | −8.6° |
| 15 | O | Me | 4-$NO_2$—Bn—O | R | 189.9–190.0 | −9.1° |
| 16 | O | Me | $F_3C-CH=CH-CH_2-O$ | R,trans | 120.8–121.1 | −8.7° |
| 17 | O | Me | $CH_3-(CH_2)_3-O$ | R | 92.1–92.2 | −10.0° |
| 18 | O | Me | $CH_3-O-(CH_2)_2-O$ | R | 94–95 | −9.7° |
| 19 | O | Me | $CH_2=CH$ | R | 79.2–79.4 | −5.4° |
| 20 | O | Me | $F_3C-CHOH-CH_2-CH=CH$ | 4R,5R,trans | 141.1–141.6 | +15.8° |
| 21 | O | Me | $F_3C-CHOH-CH_2-CH=CH$ | 4R,5S,trans | 130.1–130.3 | +21.2° |
| 22 | O | Me | $F_3C-CHOH-(CH_2)_3$ | 4R,5R | 129.0–129.4 | +4.9° |
| 23 | O | Me | $F_3C-CHOH-(CH_2)_3$ | 4R,5S | 111.3–111.7 | +19.8° |
| 24 | O | H | $F_3C-CHOH-(CH_2)_3$ | 4R,5R | 135.1–136.2 | 0.0°** |
| 25 | O | Me | Ph—CH=CH | R,trans | 167.2 | +2.7 |
| 26 | O | Me | Ph—CH=CH | R,cis | 53–58 | −3.1° |
| 27 | O | Me | Ph—$CH_2$—$CH_2$ | R | 88.0–88.2 | −8.9° |
| 28 | O | Me | $F_3C-(CH_2)_2-CH=CH$ | R,cis | 67.0 | −7.4° |
| 29 | O | Me | $F_3C-(CH_2)_2-CH=CH$ | S,cis | 67.1–67.8 | +6.9° |
| 30 | O | Me | $F_3C-(CH_2)4$ | R | 76.7–76.8 | −7.9° |
| 31 | O | Me | $F_3C-(CH_2)4$ | S | 71.6–72.1 | +7.8° |
| 32 | S | Me | Bn—O | R | 104–105 | −10.2°** |
| 33 | S | Me | Bn—O | S | 105–106 | +9.9°** |
| 34 | S | Me | $F_3C-CHOH-(CH_2)_2-O$ | 3R,5R | 80–82 | +14.9°** |
| 35 | S | Me | $F_3C-CHOH-(CH_2)_2-O$ | 3R,5S | 98–99 | +35.2°** |
| 36 | S | Me | $F_3C-(CH_2)_3-O$ | R | 79–80 | −9.7°** |
| 37 | S | Me | $F_3C-(CH_2)_3-O$ | S | 78–79 | +8.9°** |
| 38 | NMe | Me | H—O | R | 50–55 | −32.8°** |
| 39 | NMe | Me | H—O | S | 50–55 | +33.8°** |
| 40 | NMe | Me | Bn—O | R | 116–117 | −26.1°** |
| 41 | NMe | Me | Bn—O | S | 116–117 | +26.1°** |
| 42 | NMe | Me | $F_3C-(CH_2)_3-O$ | R | 104–105 | −21.8°** |
| 43 | NMe | Me | $F_3C-(CH_2)_3-O$ | S | 103–104 | +25.6°** |
| 44 | NMe | Me | $F_3C-CHOH-(CH_2)_2-O$ | 3R,5R | 135–136 | 0.0°** |
| 45 | NMe | Me | $F_3C-CHOH-(CH_2)_2-O$ | 3R,5S | 98–100 | +48.0°** |
| 46 | NH | Me | $F_3C-(CH_2)_3-O$ | R | 184.7–185.0 | −10.5°* |
| 47 | NH | Me | $F_3C-(CH_2)_3-O$ | S | 184.9–185.3 | +11.6°* |

*c = 1; dimethyl sulphoxide
**c = 1; methanol

The compounds of the invention formed the subject of pharmacological tests permitting the determination of their inhibitory power with respect to monoamine oxidase A and monoamine oxidase B.

The MAO-A and MAO-B activities in vitro were measured using a rat brain homogenate as enzyme source according to the method described by C. Fowler and M. Strolin-Benedetti in J. Neurochem, 40, 1534–1541 (1983).

The standard assay consists in homogenizing the rat brain in 20 volumes of 0.1M phosphate buffer (pH=7.4) and in preincubating 100 µl of homogenate (5 mg of tissue) at 37° C. for 20 minutes in the absence or in the presence of various concentrations of the inhibitor tested. The reaction is started by the addition of [$^{14}$C]serotonin ([$^{14}$C]5HT, final concentration 125 µM) to measure the MAO-A activity or of [$^{14}$C]phenylethylamine ([$^{14}$C]PEA, final concentration 8 µM) to measure the MAO-B activity, in a final volume of 500 µl. After incubation for 5 minutes in the case of [$^{14}$C]5HT and for 1 minute in the case of [$^{14}$C]PEA, the reaction is terminated by addition of 200 µl of 4N hydrochloric acid. The radioactive metabolites obtained from the oxidative deamination are then separated from the unconverted substrate by extraction into an organic phase, and are quantified by counting the radioactivity.

The inhibitory activities with respect to MAO-A and MAO-B are given, respectively, by the inhibition constants Ki (MAO-A) and Ki (MAO-B).

For the compounds of the invention, the Ki (MAO-A) values vary between 15 nM and more than 1 μM and the Ki (MAO-B) values vary between 1 nM and more than 1 μM.

Certain compounds of the invention are selective inhibitors of MAO-B, it being possible for the ratio Ki(MAO-A)/Ki(MAO-B) to be of the order of $10^{3.}$ Other compounds are, however, mixed inhibitors of MAO-A and MAO-B, it being possible for the ratio Ki(MAO-A)/Ki(MAO-B) to be less than 10.

The results obtained show that the compounds of the invention can be used for the preparation of drugs which are selective inhibitors of MAO-B or mixed inhibitors of MAO-A and MAO-B, these drugs finding their therapeutic application, in particular, in the treatment of depressive states of any kind, senile depressive psychoses, hypobulia, social phobias, mood disorders, in the improvement of general cerebral performance, in the prevention or treatment of neurodegenerative diseases such as Parkinson's disease, Alzheimer's disease and all memory disorders, in anxiety, in panic attacks, in the treatment of dependency and withdrawal in connection with the consumption of tobacco, alcohol and/or narcotics, and loss of appetite.

The compounds of the invention can be provided, in combination with excipients, in the form of compositions formulated for oral, parenteral or rectal administration, for example in the form of plain tablets, coated tablets, capsules, solutions, suspensions or suppositories.

Orally, the daily dose of active principle administered may be up to 50 mg/kg, in one or more individual doses. Parenterally and rectally, it may be up to 10 mg/kg, in one or more individual doses.

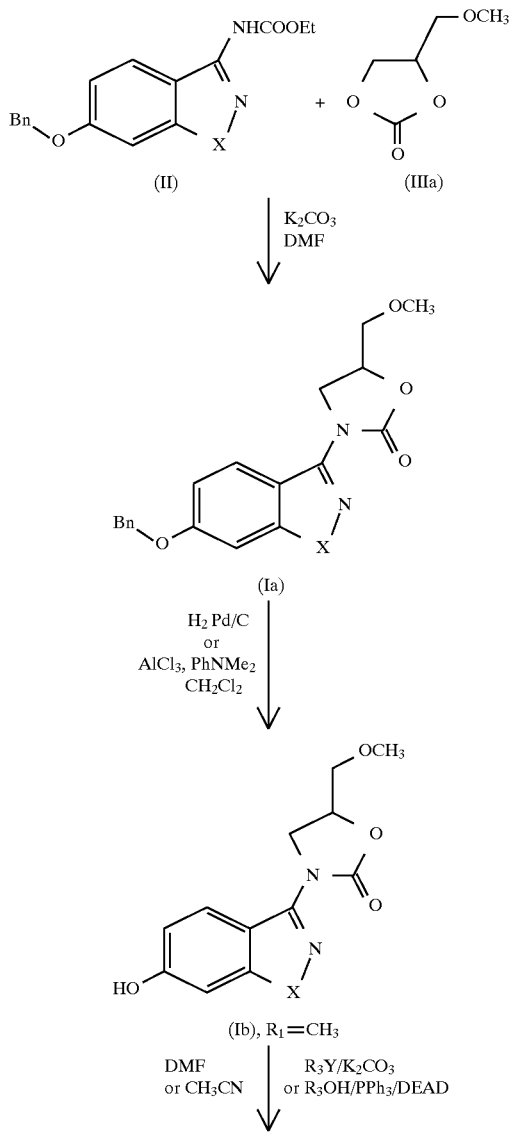

-continued
Scheme 1
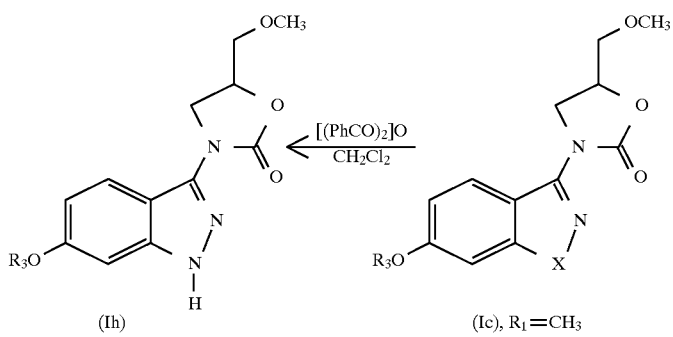
Scheme 2
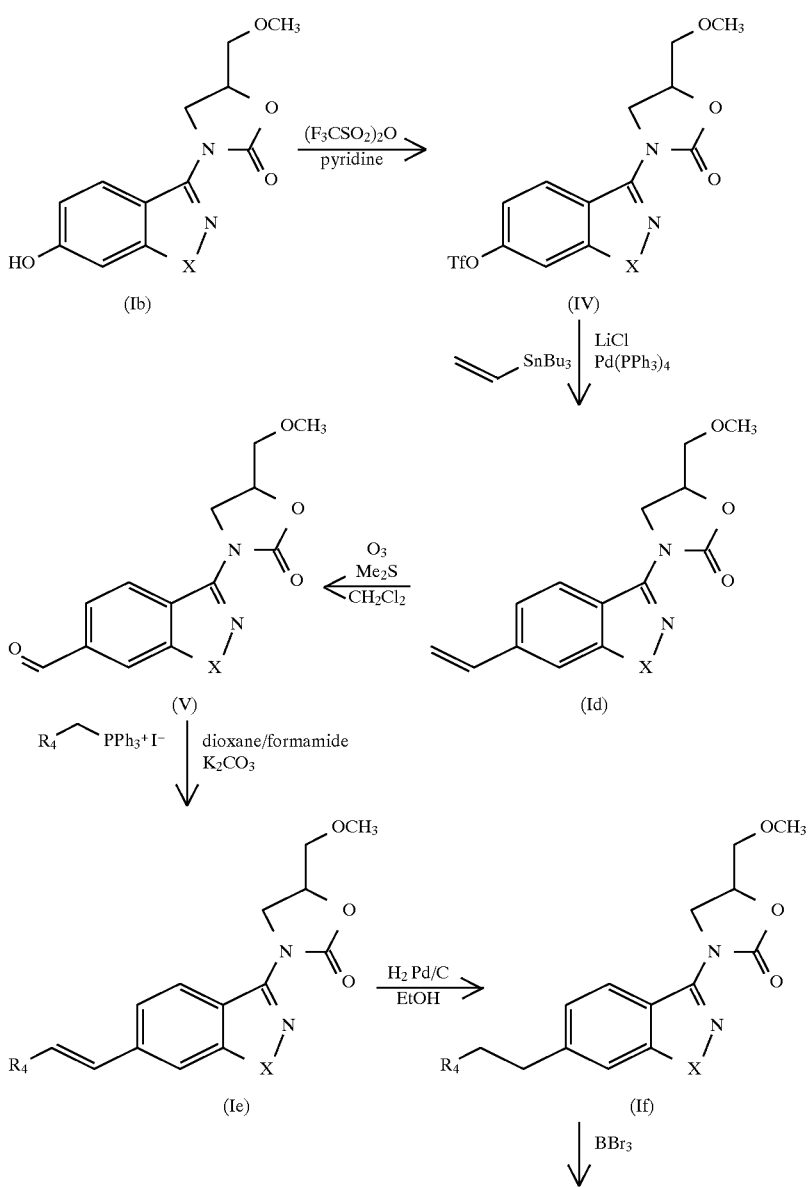

-continued
Scheme 2
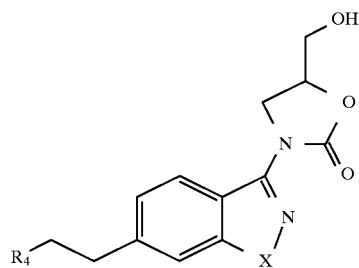
Scheme 3
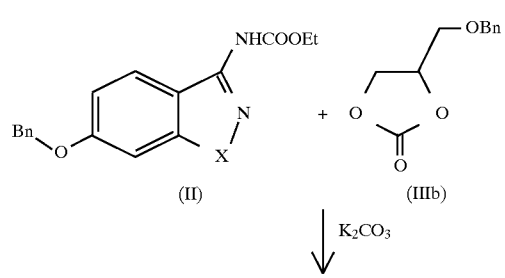
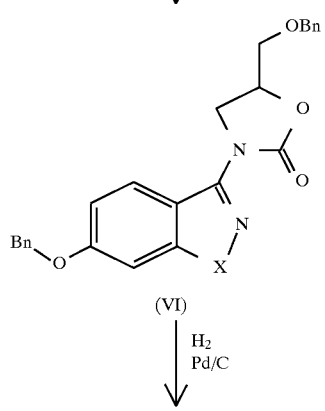
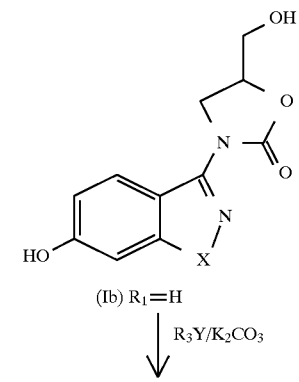
(Ib) R₁=H
R₃Y/K₂CO₃
-continued
Scheme 3
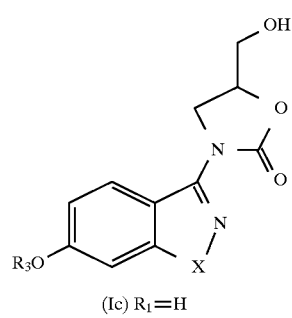
(Ic) R₁=H
Scheme 4
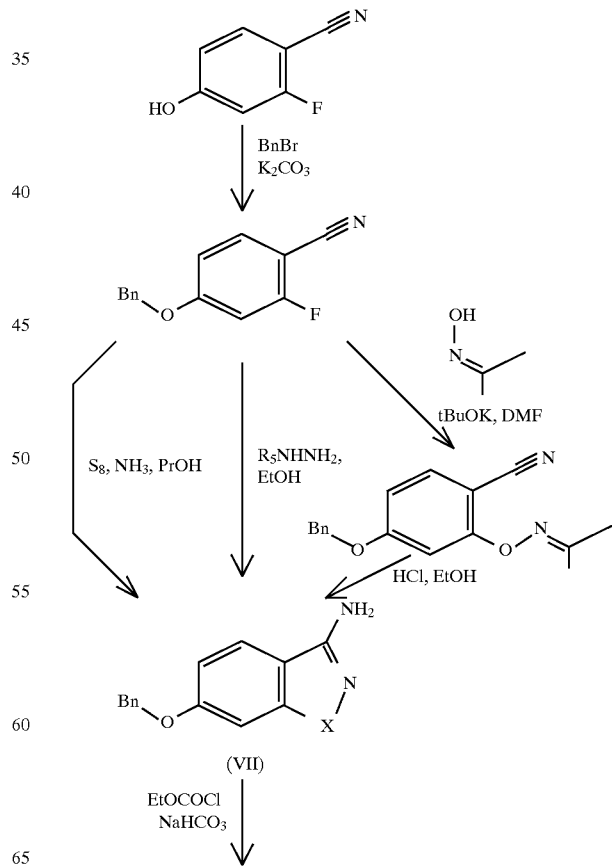
(VII)
EtOCOCl
NaHCO₃

-continued
Scheme 4

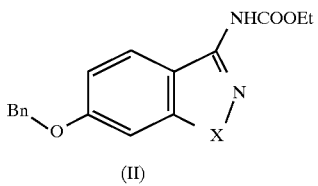

(II)

We claim:
1. 5-(Hydroxymethyl)oxazolidin-2-one derivatives of general formula (I)

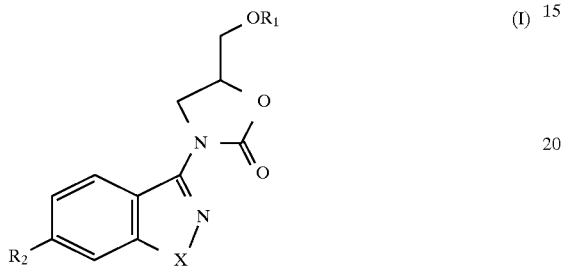

in which:
X represents an oxygen atom, a sulphur atom or a group NR, R being a hydrogen atom or a linear or branched $C_1$–$C_4$ alkyl chain,
$R_1$ represents a hydrogen atom or a methyl group, and
$R_2$ represents:
  (i) a group $R_3O$ in which $R_3$ represents alternatively a hydrogen atom, or a benzyl group which is optionally substituted with a halogen atom or with a nitro or methylenedioxy group, or represents a methoxyethyl, butyl, 4,4,4-trifluorobutyl, 4,4,4-trifluoro-3-hydroxybutyl or 4,4,4-trifluorobut-2-enyl group, or
  (ii) a group —CH=CH—$R_4$ or —$CH_2$—$CH_2$—$R_4$, in which $R_4$ represents a hydrogen atom or a phenyl, 3,3,3-trifluoropropyl or 3,3,3-trifluoro-2-hydroxypropyl group,
in the form of enantiomers or diastereoisomers, or of mixtures of these various forms, including racemic mixtures.

2. 5-(Hydroxymethyl)oxazolidin-2-one derivatives of the general formula (I) according to claim 1 in which:
X represents an oxygen atom, a sulphur atom or a group NR, R being a hydrogen atom or a linear or branched $C_{1-C4}$ alkyl chain,
$R_1$ represents a methyl group or a hydrogen atom, and
$R_2$ represents a group $R_3O$ in which $R_3$ represents alternatively a hydrogen atom, or a benzyl group which is optionally substituted with a halogen atom or with a nitro or methylenedioxy group, or represents a methoxyethyl, butyl, 4,4,4-trifluorobutyl, 4,4,4-trifluoro-3-hydroxybutyl or 4,4,4-trifluorobut-2-enyl group,
in the form of enantiomers or diastereoisomers, or of mixtures of these various forms, including racemic mixtures.

3. 5-(Hydroxymethyl)oxazolidin-2-one derivatives of the general formula (I) according to claim 1 in which:
X represents an oxygen atom, a sulphur atom or a group NR, R being a hydrogen atom or a linear or branched $C_{1-C4}$ alkyl chain,
$R_1$ represents a methyl group or a hydrogen atom, and
$R_2$ represents a group —CH=CH—$R_4$ or —$CH_2$—$CH_2$—$R_4$, in which $R_4$ represents a hydrogen atom, or a phenyl, 3,3,3-trifluoropropyl or 3,3,3-trifluoro-2-hydroxypropyl group, in the form of enantiomers or diastereoisomers, or of mixtures of these various forms, including racemic mixtures.

4. 5-(Hydroxymethyl)oxazolidin-2-one derivatives of the general formula (I) according to claim 1 in which:
X represents an oxygen atom,
$R_1$ represents a methyl group or a hydrogen atom, and
$R_2$ represents:
  (i) a group $R_3O$ in which $R_3$ represents alternatively a hydrogen atom, or a benzyl group which is optionally substituted with a halogen atom or with a nitro or methylenedioxy group, or represents a methoxyethyl, butyl, 4,4,4-trifluorobutyl, 4,4,4-trifluoro-3-hydroxybutyl or 4,4,4-trifluorobut-2-enyl group, or
  (ii) a group —CH=CH—$R_4$ or —$CH_2$—$CH_2$—$R_4$, in which $R_4$ represents a hydrogen atom, or a phenyl, 3,3,3-trifluoropropyl or 3,3,3-trifluoro-2-hydroxypropyl group,
in the form of enantiomers or diastereoisomers, or of mixtures of these various forms, including racemic mixtures.

5. 5-(Hydroxymethyl)oxazolidin-2-one derivatives of the general formula (I) according to claim 1 in which:
X represents an oxygen atom,
$R_1$ represents a methyl group or a hydrogen atom, and
$R_2$ represents alternatively a hydroxyl group, or a phenylmethoxy group which is optionally substituted with a halogen atom or with a nitro or methylenedioxy group, or represents a 4,4,4-trifluorobutoxy group or a 4,4,4-trifluoro-3-hydroxybutoxy group,
in the form of enantiomers or diastereoisomers, or of mixtures of these various forms, including racemic mixtures.

6. (S)-5-Methoxymethyl-3-[6-(4,4,4-trifluorobutoxy)-1,2-benzisoxazol-3-yl]oxazolidin-2-one.

7. Process for the preparation of compounds of formula (I)

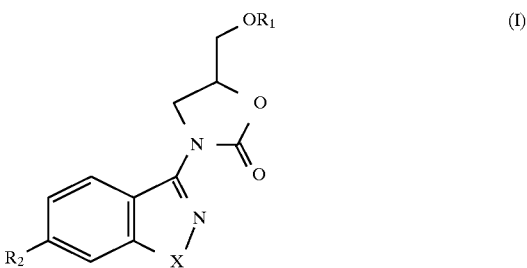

in which:
X represents an oxygen atom, A sulphur atom or a group NR, R being a hydrogen atom or a linear or branched $C_{1-C4}$, alkyl chain,
$R_1$ represents a methyl group, and
$R_2$ represents a group $R_3O$ in which $R_3$ represents alternatively a hydrogen atom, or a benzyl group which is optionally substituted with a halogen atom or with a nitro or methylenedioxy group, or represents a methoxyethyl, butyl, 4,4,4,-trifluorobutyl, 4,4,4-trifluoro-3-hydroxybutyl or 4,4,4-trifluorobut-2-enyl group, characterized in that the compound of formula II

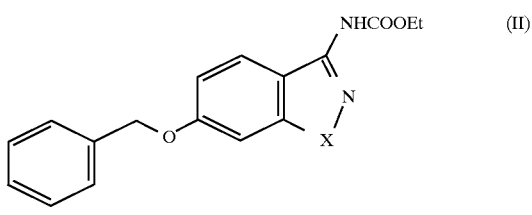

is treated with one of the 4(R) or 4(S) isomers of 4-methoxymethyl-1,3-dioxolan-2-one of formula (IIIa)

in the presence of potassium carbonate in order to obtain the 5 (S) or 5(R) isomer of the compound of formula (Ia)

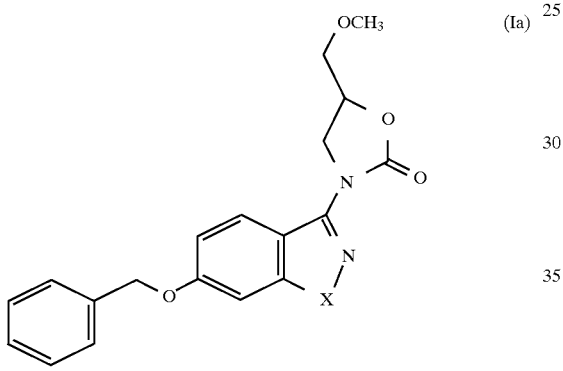

which is debenzylated by catalytic hydrogenation or with the aid of a Lewis acid in order to obtain the 5(S) or 5(R) isomer of the compound of formula ((Ib), $R_1=CH_3$)

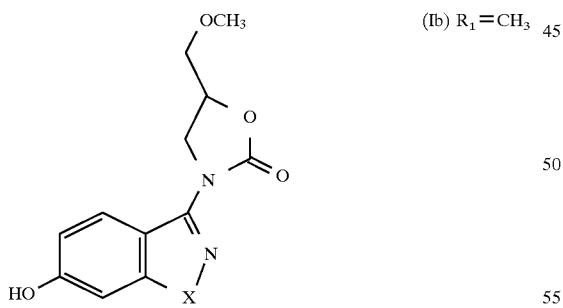

which is treated either with a compound of formula $R_3Y$ in which $R_3$ is defined as in formula (I), with the exception of the meanings hydrogen and unsubstituted benzyl, and Y is a leaving group, in the presence of potassium carbonate, or with a compound of formula $R_3OH$ in which $R_3$ is defined as in formula (I), with the exception of the meanings hydrogen unsubstituted benzyl, in the presence of triphenylphosphine and diethyl azodicarboxylate, in order to obtain the 5(S) or 5(R) isomers of the compounds of formula ((Ic) $R_1=CH_3$)

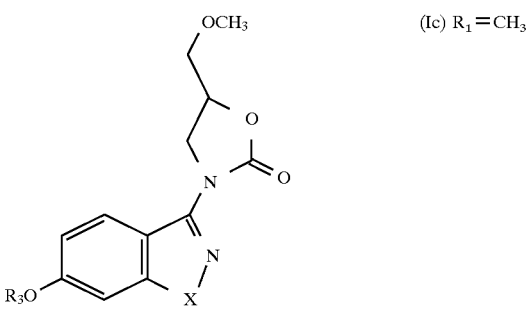

and, if necessary, the compounds in which $X=NCH_3$ are treated with benzoyl peroxide in order to obtain the compounds of formula (Ih) in which $X=NH$

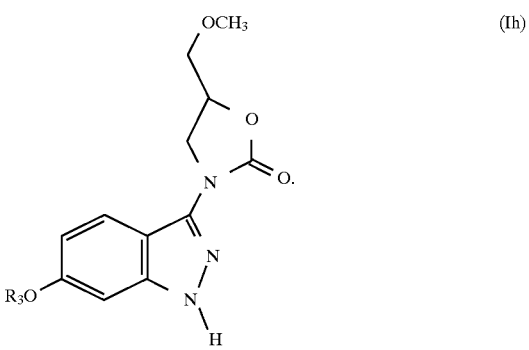

8. Process for the preparation of compounds of formula (I)

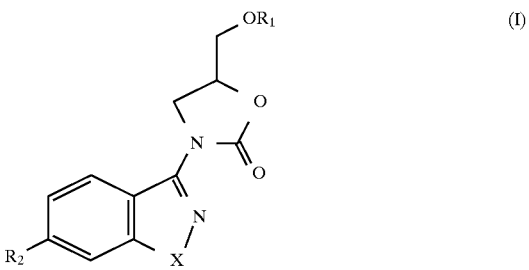

in which:

X represents an oxygen atom, a sulphur atom or a group NR, R being a hydrogen atom or a linear or branched $C_1-C_4$ alkyl chain $R_1$ represents a hydrogen atom, and $R_2$ represents a group $R_3O$ in which $R_3$ represents alternatively hydrogen atom, or a benzyl group which is optionally substituted with a halogen atom or with a nitro or methylenedioxy group, or represents a methoxyethyl, butyl, 4,4,4,-trifluorobutyl, 4,4,4-trifluoro-3-hydroxybutyl or 4,4,4-trifluorobut-2-group, characterized in that ethyl 6-phenylmethoxy-1,2-benzisoxazole-3-carbamate of formula (II)

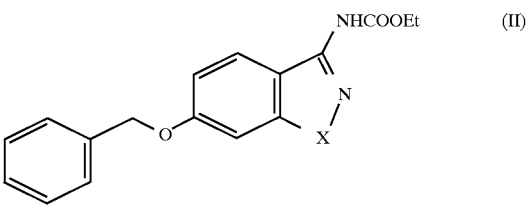

is treated with one of the 4(S) or 4(R) isomers of 4-phenylmethoxymethyl-1,3-dioxolan-2-one of formula (IIIb)

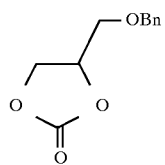  (IIIb)

in the presence of potassium carbonate in order to obtain the 5(R) or 5(S) isomer of the compound of formula (VI)

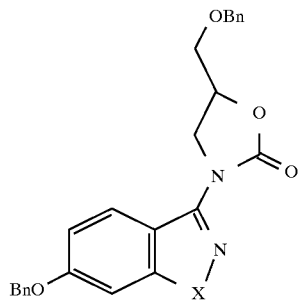  (VI)

which is debenzylated by catalytic hydrogenation in order to obtain the 5(R) or 5(S) isomer of the compound of formula ((Ib) $R_1$=M)

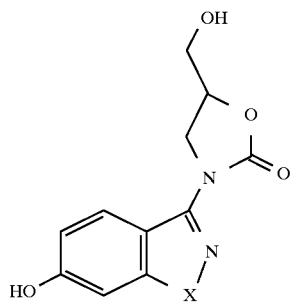  (Ib) $R_1$=H which is then treated with a compound of formula $R_3Y$ in which $R_3$ is defined as in formula (I), with the exception of the meaning hydrogen, and Y is a leaving group, in the presence of potassium carbonate, in order to obtain the 5(R) or 5(S) isomers of the compounds of formula ((Ic), $R_1$=H)

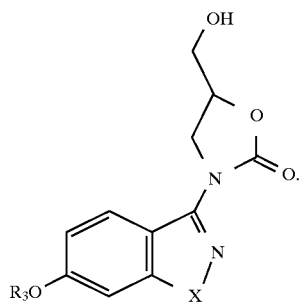  (Ic), $R_1$=H

9. Process for the preparation of compounds of formula (I)

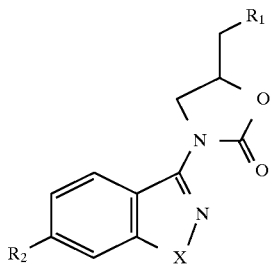  (I)

in which:

X represents an oxygen atom, a sulphur atom or a group NR, R being a hydrogen atom or a linear or branched $C_1$–$C_4$ alkyl chain, $R_1$ represents a hydrogen atom or a methyl group, and $R_1$ represents a group —CH=CH—$R_4$ or —CH$_2$—CH$_2$—$R_4$, in which $R_4$ represents a hydrogen atom, or a phenyl, 3,3,3-trifluoropropyl or 3,3,3-trifluoro-2-hydroxypropyl group, characterized in that it consists in treating the compound of formula ((Ib), $R_1$=CH$_3$)

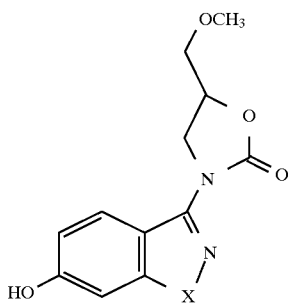  (Ib)

with trifluoromethanesulphonic anhydride, in reacting the resulting compound of formula (IV)

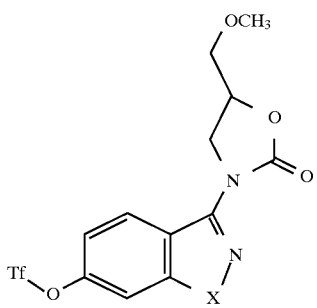  (IV)

with tributylvinyl tin in the presence of lithium chloride and tetrakis(triphenylphosphine)palladium, in treating the resulting compound of formula (Id)

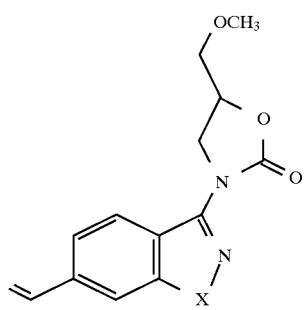(Id)

with ozone and then with dimethyl sulphide, in reacting the resulting compound of formula (V)

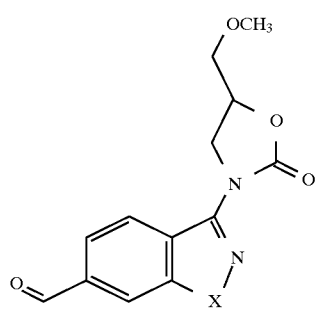(V)

with a triphenylphosphonium iodide of formula $R_4CH_2PPh_3^+I^-$ in which $R_4$ is defined as in formula (I) above, with the exception of the meaning hydrogen, in the presence of potassium carbonate, in reducing the resulting compound of formula (Ie)

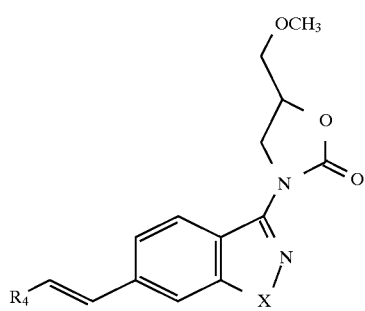(Ie)

with hydrogen in the presence of a catalyst in order to obtain the compound of formula (If)

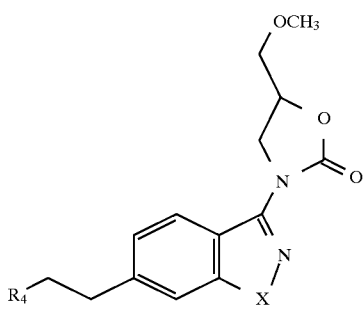(If)

in which $R_4$ is defined as above, and finally in treating the compound of formula (Id), (Ie) or (If) with boron tribromide in order to obtain the compound of formula (Ig)

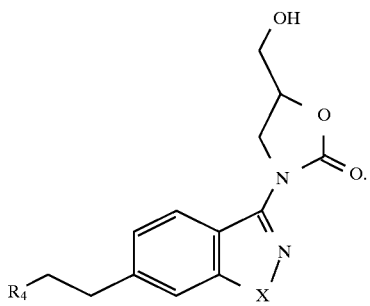(Ig)

10. Pharmaceutical composition, characterized in that it comprises a compound of formula (I) according to claim 1 in combination with any appropriate excipient.

11. A method for the treatment of depressive states, senile depressive psychoses, hypobulia, social phobias, mood disorders, general cerebral performance, neurodegenerative diseases, memory disorders, anxiety, panic attacks, dependency or withdrawal in connection with the consumption of tobacco, alcohol or narcotics, or loss of appetite, comprising administering to a patient in need thereof a therapeutically effective amount of a compound of formula (I) according to claim 1 in combination with an appropriate excipient.

* * * * *